(12) United States Patent
Jiang et al.

(10) Patent No.: US 6,207,850 B1
(45) Date of Patent: Mar. 27, 2001

(54) PROCESS FOR CO-PRODUCTION OF DIALKYL CARBONATE AND ALKANEDIOL

(75) Inventors: Zhaozhong Jiang, Thorofare; Rene B. LaPierre, Medford, both of NJ (US); Jose G. Santiesteban, Allentown, PA (US); Hye Kyung Cho Timken, Woodbury; William A. Weber, Marlton, both of NJ (US)

(73) Assignee: Mobil Oil Corporation, Fairfax, VA (US)

( * ) Notice: Subject to any disclaimer, the term of this patent is extended or adjusted under 35 U.S.C. 154(b) by 0 days.

(21) Appl. No.: 09/433,362

(22) Filed: Nov. 3, 1999

(51) Int. Cl.⁷ ............................. C07C 68/06; C07C 27/02
(52) U.S. Cl. ............................................. 558/277; 568/858
(58) Field of Search ................................................ 558/277

(56) References Cited

U.S. PATENT DOCUMENTS

| | | |
|---|---|---|
| 3,642,858 | 2/1972 | Frevel et al. . |
| 4,062,884 | 12/1977 | Romano et al. . |
| 4,181,676 | 1/1980 | Buysch . |
| 4,391,739 | 7/1983 | Chu . |
| 4,434,105 | 2/1984 | Buysch et al. . |
| 4,661,609 | 4/1987 | Knifton . |
| 4,686,274 | 8/1987 | Harris et al. . |
| 4,691,041 | 9/1987 | Duranleau et al. . |
| 4,895,970 | 1/1990 | Harris . |
| 5,015,753 | 5/1991 | Harris . |
| 5,218,135 | 6/1993 | Buysch et al. . |
| 5,231,212 | 7/1993 | Buysch et al. . |
| 5,292,980 | 3/1994 | Dessau . |
| 5,387,708 | 2/1995 | Molzahn et al. . |
| 5,391,803 | 2/1995 | King et al. . |
| 5,430,170 | 7/1995 | Urano et al. . |
| 5,436,362 | 7/1995 | Kondoh et al. . |
| 5,489,703 | 2/1996 | Pacheco et al. . |
| 5,498,743 | 3/1996 | Shih et al. . |
| 5,663,480 | 9/1997 | Tsuneki et al. . |
| 5,847,189 | 12/1998 | Tojo et al. . |

FOREIGN PATENT DOCUMENTS

| | | |
|---|---|---|
| 0 478 073 A2 | 9/1991 | (EP) . |
| 3-44354 | 2/1991 | (JP) . |
| 6-107601 | 4/1994 | (JP) . |

OTHER PUBLICATIONS

Chang, C.D., *Handbook of Heterogenous Catalysis*, Wiley–VCH:Weinheim, Germany, vol. 4, Chapter 3.7 (1997).

Yagi, F., Kanuka, N., Tsuji, H., Nakata, S., Kita, H. and Hattori, H., "$^{133}$Cs and $^{23}$Na MAS NMR studies of zeolite X containing cesium," *Microporous Materials* 9:229–235(1997).

Skibsted, J., Vosegaard, T., Bildsøe, H. and Jakobsen, H.J., "$^{133}$Cs chemical Shielding Anisotropics and Quadrupole Couplings from Magic–Angle Spinning NMR of Cesium Salts," *J. Phys. Chem.*, 100:14872–14881(1996).

Knifton, J.F. and Duranleau, R.G., "Ethylene Glycol–Dimethyl Carbonate Cogeneration," *J. of Molecular Catalysis* 67:389–399(1991).

Watanabe, Y. and Tatsumi T., "Hydrotalcite–type Materials as Catalysts for the Synthesis of Dimethyl Carbonate from Ethylene Carbonate and Methanol[1,]" *Microporous and Mesoporous Materials* 22:399–407(1998).

*Primary Examiner*—Michael G. Ambrose
(74) *Attorney, Agent, or Firm*—Malcolm D. Keen; Norby L. Foss

(57) ABSTRACT

A method is provided for co-producing dialkyl carbonate and alkanediol by reacting alkylene carbonate with alkanol in the presence of a IIIA metal oxide catalyst, preferably alumina.

10 Claims, 3 Drawing Sheets

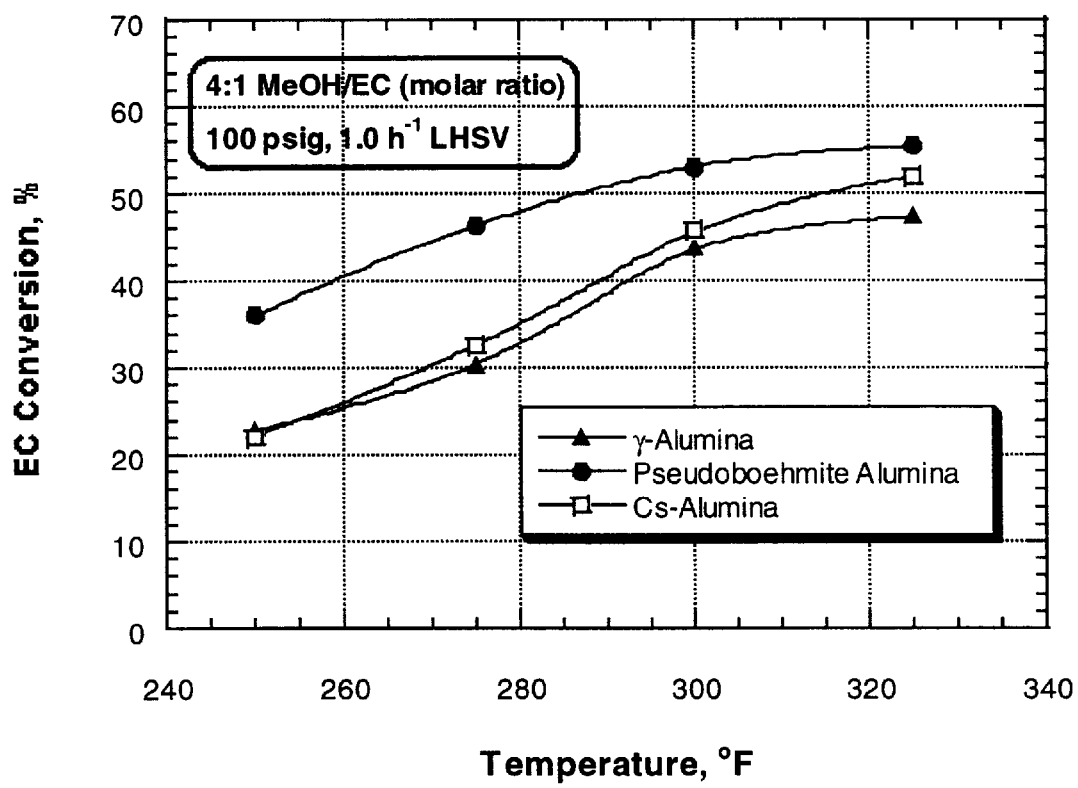
Figure 1. Ethylene Carbonate (EC) Conversion vs. Temperature for the MeOH/EC Reaction Using Pseudoboehmite Alumina, γ-Alumina, and Cs-alumina

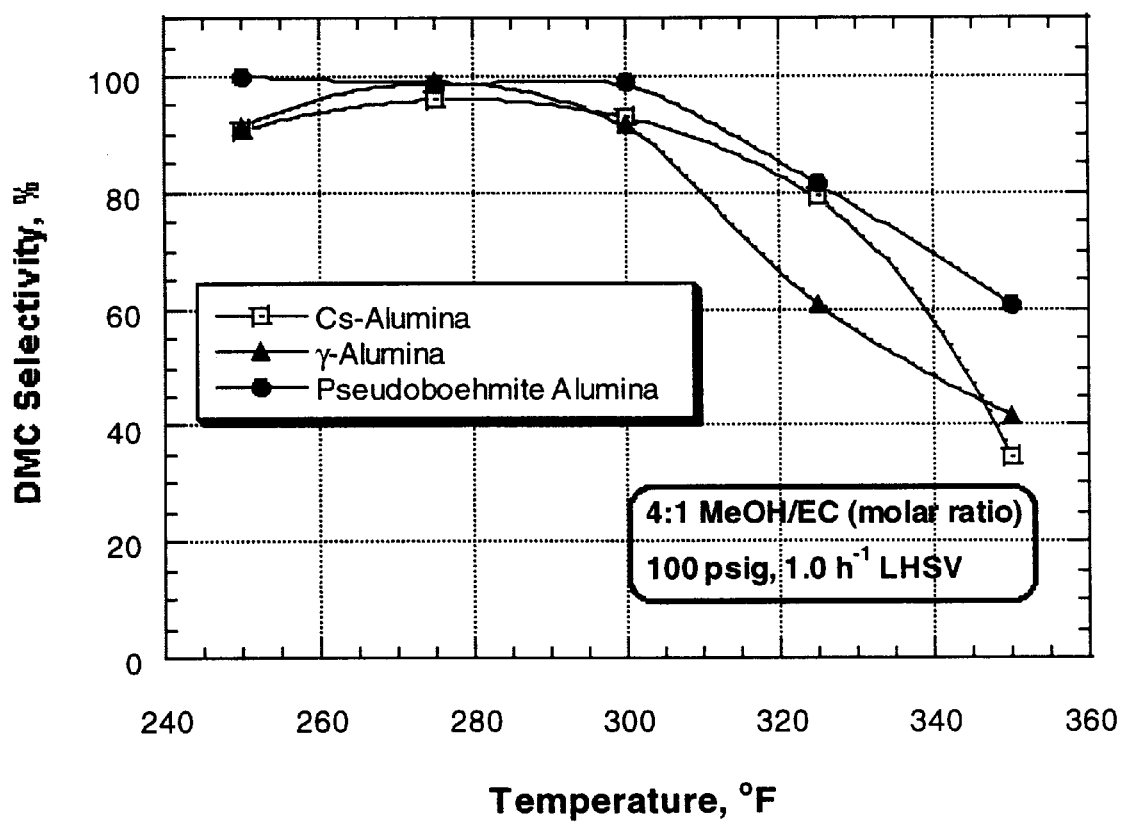
Figure 2. Dimethyl Carbonate (DMC) Selectivity vs. Temperature for the MeOH/EC Reaction Using Pseudoboehmite Alumina, γ-Alumina, and Cs-alumina

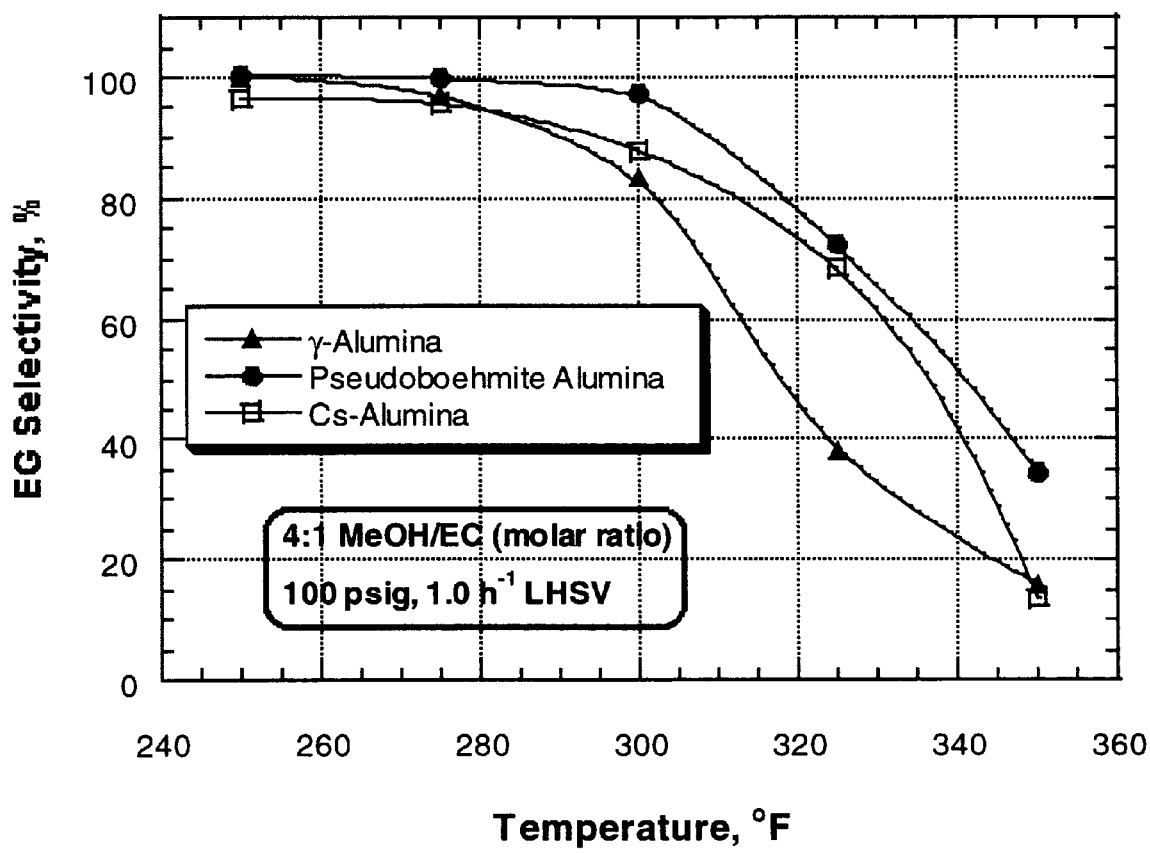
Figure 3. Ethylene Glycol (EG) Selectivity vs. Temperature for the MeOH/EC Reaction Using Pseudoboehmite Alumina, γ-Alumina, and Cs-alumina

PROCESS FOR CO-PRODUCTION OF DIALKYL CARBONATE AND ALKANEDIOL

BACKGROUND

This invention relates to a method of co-producing dialkyl carbonate and alkanediol, and, in particular, to a method for enhancing the efficiency of the co-production by the use of a IIIA metal oxide catalyst containing hydroxyl groups.

Various homogeneous catalysts have been proposed for carbonate transesterification. For example, U.S. Pat. Nos. 3,642,858 and 4,181,676 disclose the preparation of dialkyl carbonates by transesterifying alkylene carbonates with alcohols in the presence of alkali metals or alkali metal compounds without the use of a support material. U.S. Pat. No. 4,661,609 teaches the use of a catalyst selected from the group consisting of zirconium, titanium and tin oxides, salts or complexes thereof.

Commercial use of homogeneous catalysts is restricted because separation of the catalyst from the unconverted reactants and organic product can be difficult. Because the transesterification is an equilibrium reaction, in an attempt to isolate the intended dialkyl carbonate by distillation of the reaction liquid without advance separation of the catalyst, the equilibrium is broken during the distillation and a reverse reaction is induced. Thus, the dialkyl carbonate once formed reverts to alkylene carbonate. Furthermore, due to the presence of the homogenous catalyst, side reactions such as decomposition, polymerization, or the like concurrently take place during the distillation which decrease the efficiency.

Various heterogenous catalysts have also been proposed for carbonate transesterification. The use of alkaline earth metal halides is disclosed in U.S. Pat. No. 5,498,743. Knifton, et al., "Ethylene Glycol-Dimethyl Carbonate Cogeneration," *J. Molec. Catal.* 67:389–399 (1991) disclose the use of free organic phosphines or organic phosphines supported on partially cross-linked polystyrene. U.S. Pat. No. 4,691,041 discloses the use of organic ion exchange resins, alkali and alkaline earth silicates impregnated into silica, and certain ammonium exchanged zeolites. U.S. Pat. No. 5,430,170 discloses the use of a catalyst containing a rare earth metal oxide as the catalytically active component. The use of hydrotalcites is disclosed in Japanese Unexamined Patent Application 3[1991]-44,354. The use of MgO is disclosed in Japanese Unexamined Patent Application 6[1994]-107,601. The use of zeolites ion-exchanged with alkali metal and/or alkaline earth metal, thereby containing a stoichiometric amount of metal, are disclosed in U.S. Pat. No. 5,436,362.

Inorganic heterogenous catalysts generally possess thermal stability and easy regeneration. However, these catalysts, including the zeolites containing a stoichiometric amount of alkali or alkaline earth metal, generally demonstrate low activity and/or selectivity and are unsatisfactory for commercial application.

Polymer supported organic phosphines and ion exchange resins show high activity and good to excellent selectivity in transesterification reaction between alkylene carbonate and alkanol; however, these polymeric materials do not appear very stable and gradually lose catalytic activity, especially at relatively high temperatures.

Thus, there remains a need for a method of transesterifying alkylene carbonate with alkanol to co-produce dialkyl carbonate and alkanediol which will provide higher feed conversion and product selectivity over a wide temperature range.

SUMMARY OF INVENTION

A method is provided for co-producing dialkyl carbonate and alkanediol by reacting alkylene carbonate with alkanol in the presence of a IIIA metal oxide catalyst. The preferred alkylene carbonate is ethylene carbonate and the preferred alkanol is methanol.

The preferred metal oxide of the catalyst is alumina. It is also preferred that the catalyst contain hydroxyl groups. The hydrated catalyst will usually contain hydroxyl groups in an amount greater than 0.1 wt % and less than 30 wt % of the catalyst. Another preferred embodiment includes the catalyst having an octahedral structure. The catalyst can further include an inert catalyst support.

The alumina catalyst is preferably prepared through dehydration of aluminum trihydroxide or aluminum monohydroxide, such as pseudoboehmite.

The process conditions include a reaction temperature of about 20° C. (68° F.) to about 300° C. (572° F.), a reaction pressure of about 14 to about 4000 psig, a liquid hour space velocity of about 0.1 to 40 $hr^{-1}$, and a molar ratio of alkanol to alkylene carbonate of about 1–20.

Unlike polymer catalysts such as ion exchange resins, the IIIA metal oxide catalysts used in the method of the invention are thermally stable and regenerable. The combination of high catalytic activity and selectivity in a wide temperature range, and excellent thermal stability and regenerability of the catalysts, render them suitable for commercial use in co-producing organic carbonate and alkanediol through ester exchange reaction. Also, the general availability and low cost of alumina catalysts could significantly improve the process economics.

The organic carbonates produced by the method of the invention, dimethyl carbonate in particular, have potential application as "green" replacements for phosgene that is used mainly in manufacture of polyurethane and polycarbonate resins.

BRIEF DESCRIPTION OF DRAWINGS

FIG. 1 is a graph demonstrating EC (ethylene carbonate) conversion vs. temperature for the MeOH/EC reaction using pseudoboehmite alumina, γ-alumina, and Cs-alumina as the catalysts.

FIG. 2 is a graph demonstrating DMC (dimethyl carbonate) selectivity vs. temperature for the MeOH/EC reaction using pseudoboehmite alumina, γ-alumina, and Cs-alumina as the catalysts.

FIG. 3 is a graph demonstrating EG (ethylene glycol) selectivity vs. temperature for the MeOH/EC reaction using pseudoboehmite alumina, γ-alumina, and Cs-alumina as the catalysts.

DETAILED DESCRIPTION OF INVENTION

In accordance with the present invention, a method is provided for the co-production of dialkyl carbonate and alkanediol through the transesterification of alkylene carbonate with alkanol using a IA metal oxide catalyst.

Generally, all alkylene carbonates can be used as a reactant in this invention. However, low molecular weight alkylene carbonate such as ethylene carbonate, propylene carbonate, butylene carbonate or the like is preferred; ethylene carbonate or propylene carbonate is most preferred.

Generally, all alkanol reactants can be used, provided the alkanol reacts with cyclocarbonate to produce the dialkyl carbonate and alkanediol product. However, an aliphatic or aromatic alkanol having 1 to 10 carbon atoms is preferably used. For example, methanol, ethanol, n-propanol, iso-propanol, n-butanol, iso-butanol, secondary butanol, tertiary butanol, allyl alcohol, pentanol, cyclo-hexanol, benzyl alcohol, 2-phenyl ethyl alcohol, 3-phenyl propyl alcohol, 2-methoxy ethanol or the like can be used as the aliphatic or aromatic alcohol. A lower aliphatic alcohol such as methanol is most preferably used due to its reactivity and low cost.

Further, a phenolic compound can be used in place of the alcoholic compound as the compound which has a hydroxyl (OH) group and reacts with cyclocarbonate to produce the carbonate.

The catalyst used in the method of the invention is a IIIA metal oxide catalyst. The metal is chosen from the IIIA metals listed on the Periodic Table of elements. Aluminum, gallium, and indium are preferred IIIA metals. Aluminum is most preferred, making alumina the preferred oxide. The catalyst used in the method of the invention will contain only a single metal and, therefore, will not contain a mixed metal oxide. The IIIA metal oxide is the active component and can be supported on any known catalyst support.

In a preferred embodiment, the catalyst used in the method of the invention contains hydroxyl groups. Hydroxyl group content is defined by the weight of hydroxyl group versus the total weight of the catalyst. A large portion of these hydroxyl groups generally reside on the surface of the catalyst. The hydrated catalyst will usually contain hydroxyl groups in an amount greater than 0.1 wt % and less than about 30 wt % of the catalyst; preferably between about 0.3 and 15 wt % of the catalyst. It is believed that the presence of the hydroxyl groups contributes to a higher activity of the catalyst.

Most of the commercial catalysts of the type used in the method of the invention, such as γ-alumina, have a surface area of about 200–300 m$^2$/g. A high surface area is preferred in the method of the invention, with no specific upper limit. The catalysts used in the method of the invention typically have a surface area of between about 5–600 m$^2$/g. A surface area above 50 m$^2$/g is preferred.

The IIIA metal oxide catalyst will generally have octahedral or a mixture of octahedral and tetrahedral configuration. Tetrahedral configuration means that the IIIA metal, such as aluminum, is coordinated with four oxygen atoms and forms a tetrahedral geometric structure. Octahedral configuration means that the IIIA metal is coordinated with six oxygen atoms, thereby forming an octahedral structure. Penta-coordinated oxides do exist. However, they are mainly formed during a transition from a octahedral to tetrahedral configuration, such as when an oxide material is being dehydrated. The penta-coordinated configuration is usually present in a relatively small quantity, if at all, in the final IIIA metal oxide catalyst.

It is preferred that the catalyst used in the method of the invention contain a metal, e.g. aluminum, in octahedral form. Potential catalysts and catalyst precursors that can be utilized in the method of the invention are aluminum trihydroxides such as Gibbsite, Bayerite, and Nordstrandite which can be described as a chemical formula, $Al_2O_3 \cdot 3H_2O$; and aluminum monohydroxides such as Boehmite, Pseudoboehmite, Diaspore which can be described as a chemical formula, $Al_2O_3 \cdot H_2O$. These materials are also favored because they contain a high hydroxyl content. Among aluminum monohydroxides, Pseudoboehmite (fine boehmite) is desirable for its high surface area and excellent retention of surface area upon calcination. In addition, transient alumina with a high surface area is appropriate for this application, which includes alumina in Gamma, Eta, Delta, Chi, and Theta forms. The nomenclature, structure and transformation of alumina phases have been published by W. H. Gitzen, "Alumina As a Ceramic Material," American Ceramic Society, Inc, Columbus, Ohio, (1970); J. W. Newsome, et al., "Alumina Properties, Technical Paper No. 10," Alcoa Chemical Company of America, Pittsburgh, Pa, (1960), and are incorporated herein by reference.

The IIIA metal oxide catalyst can also contain alkali metal, alkaline earth metal, or a combination thereof. Alkali metal and alkaline earth metal are both defined to include compounds containing these metals. The specific limits of the amount of alkali and/or alkaline earth metal which can be incorporated into the catalyst can be determined by one skilled in the art, and will vary based upon the specific catalyst and alkali and/or alkaline earth metal used. The amount of alkali and/or alkaline earth metal in the catalyst should not exceed an amount where the pore space of the catalyst is significantly restricted, thereby decreasing the surface area of the catalyst and its activity. For example, if cesium is used as the alkali metal, the amount of cesium will typically be between about 3–50 wt % of the catalyst. Alkali and/or alkaline earth metal may be incorporated into the alumina catalyst by any known means, such as incipient wetness impregnation method.

The reactor type in this invention can be any type generally known, such as a continuous fluid bed, fixed bed or stirred tank, etc. With the heterogenous catalyst used in the method of the invention, it is preferred that a fixed bed be used so as to avoid the expense of having to recover the catalyst from the reagents and product.

The reaction conditions of this invention include a reaction temperature of about 20° C. to about 300° C., preferably about 60° C. to about 175° C.; a reaction pressure of about 14 to about 4000 psig, preferably about 50 to about 400 psig; a liquid hour space velocity of about 0.1 to about 40 hr$^{-1}$, preferably about 0.5 to about 10 hr$^{-1}$; and a molar ratio of alkanol to alkylene carbonate of about 1 to 20, preferably about 2 to 8.

The following comparative examples are provided to assist in a further understanding of the invention. The particular materials and conditions employed are intended to be further illustrative of the invention and are not limiting upon the reasonable scope thereof.

EXAMPLE 1

This example describes a method for preparing three catalysts employed in the examples.

Three catalysts employed were: pseudoboehmite (fine particle boehmite) alumina, γ-alumina (prepared from the pseudoboehmite alumina via calcination at 538° C.), and Cs-containing alumina. Boehmite is a form of alumina with molecular formula $(AlO-OH)_n$. The physical properties of the three alumina samples are shown in Table 1.

TABLE 1

| Catalyst | BET Surface Area (m$^2$/g) | H Content[a] (millimole/g) | OH, wt %[b] |
| --- | --- | --- | --- |
| Pseudoboehmite alumina | 356 | 3.7 | 6.3 |
| γ-alumina | 263 | 1.8 | 3.1 |
| Cs-alumina | 101 | 1.2 | 2.0 |

[a]H content determined by proton MAS NMR after samples were dried at 100° C. for 12 hours under vacuum. See Example 2 for details.
[b]OH wt % calculated from H content.

The pseudoboehmite alumina, a commercial sample, was pelleted and sized to 80–120 mesh prior to catalyst evaluation.

The γ-alumina was prepared by mulling the commercial pseudoboehmite alumina powder with water to form uniform extrudable mixture and formed into ⅛" cylindrical shape extrudates using a standard augur extruder. The extrudates were dried on a belt filter at 250° F. (121 ° C) and calcined under air at 1000° F. (538° C) for 3 hours. X-ray powder diffraction showed the phase was converted to the gamma form. The extrudate sample was sized to 80–120 mesh prior to catalyst evaluation.

The Cs-alumina catalyst was prepared from the above pseudoboehmite extrudate after drying. Dried alumina extrsdates were impregnated with 22% Cs using a solution containing cesium carbonate via incipient wetness impregnation method. The Cs impregnated alumina extrudates were dried at 250° F. (121° C.) overnight and calcined under air at 1000° F. (538° C.) for 3 hours. The calcined Cs-alumina sample contained 22.2 wt % Cs and was sized to 80–120 mesh prior to catalyst evaluation.

EXAMPLE 2

This example describes the NMR characterization of the structures and H content of three alumina catalysts; pseudoboehmite, γ-alumina, and Cs-alumina.

500.13 MHZ proton MAS NMR spectra were obtained on a Bruker AMX spectrometer using 12–15 kHz sample spinning, 2.7 $\mu$s pulses, and a 30s recycle time. Chemical shifts are referenced to external TMS at 0.0 ppm. The samples were prepared for proton NMR experiments by drying at 100° C. (to remove physisorbed water) under vacuum for 12 hours. An 83.8/16.2 mixture of $D_2O$ (99% deuterated) and $H_2O$ was used as the absolute $^1H$ quantitation standard. The results are summarized in Table 1.

130.33 MHZ $^{27}Al$ MAS NMR spectra were obtained on a 500 MHZ Bruker AMX spectrometer using 4.0–4.5 kHz sample spinning, 0.8 $\mu$s excitation pulses, an 80 ms recycle time, and high power proton decoupling. 1M $Al(NO_3)_3$ was the external chemical shift reference.

The pseudoboehmite catalyst is an alumina hydrate containing exclusively octahedral aluminum (surrounded by six oxygen) and high concentration of hydroxyl groups. γ-alumina, on the other hand, contains tetrahedral and penta-coordinated aluminum in addition to octahedral aluminum, and low concentration of hydroxyl groups.

The $^{27}Al$ NMR spectrum of the pseudoboehmite showed a single peak at 5.4 ppm due to octahedral aluminum while three $^{27}Al$ resonance peaks at 5.4, 28.0, and 62.1 ppm corresponding to octahedral, penta-coordinated, and tetrahedral aluminum, respectively, were observed for γ-alumina. Cs-alumina exhibited two absorbtions at 5.4 and 62.1 ppm due to corresponding octahedral and tetrahedral aluminum.

EXAMPLE 3

Transesterification evaluations were performed using each of the catalysts described in Example 1.

The transesterification evaluations were performed in a fixed bed microunit equipped with a three-zone furnace and a down-flow trickle-bed tubular reactor (½" ID). Catalyst powder was pelletized and sized to 80–120 mesh, and the reactor was loaded with 10 cc of the sized catalyst.

After pressure testing of the unit, the catalyst was dried at 400 ° F. for two hours under 1 atmosphere, 170 cc/min nitrogen flow. At the end of this period, the reactor was cooled down to 150° F. (66° C.) and nitrogen flow was stopped. The reactor pressure, controlled by a pressure regulator, was then set to 100 psi, and the EC/methanol mixture feed was pumped and added to the top of the reactor at 1.0 $h^{-1}$ LHSV. The reactor temperature was gradually increased to initial operating temperature (250° F.) (121° C). Each material balance was typically started after the reactor was conditioned for eight hours. Liquid products were condensed in a stainless steel dropout pot at −10° C. Both liquid and off-gas products were analyzed by GC. The catalytic reaction was studied at various temperatures and LHSV to vary EC conversion.

The three alumina catalysts were evaluated according to the procedures described above. Detailed operating conditions, material balance data, and results on EC conversion and dimethyl carbonate (DMC)/ethylene glycol (EG) selectivities for pseudoboehmite alumina, γ-alumina, and Cs-alumina, are summarized in Tables 2, 3, and 4, respectively.

Feed conversion is calculated based on EC converted during the transesterification reaction since an excessive amount of methanol (relative to EC) was used for all reactions. During EC/MeOH reaction, 2-hydroxyethyl methyl carbonate (HEMC) intermediate was also formed in addition to DMC and EG. The concentration of HEMC varies depending on the reaction conditions. Since it is recyclable along with unreacted EC, the intermediate carbonate is not considered as a byproduct. The feed conversion and product selectivity are defined as follows:

EC Conversion=(EC converted to products other than HEMC)/(total EC in feed)

DMC Selectivity=(moles of DMC formed)/(moles of EC converted to products other than HEMC)

EG Selectivity=(moles of EG formed)/(moles of EC converted to products other than HEMC).

TABLE 2

Transesterification of Ethylene Carbonate with Methanol Catalyzed by Pseudoboehmite Alumina (Condition: 100 psig)

| Temperature, ° F./° C. | 250/121 | 275/135 | 300/149 | 325/163 | 350/177 | 325/163 | 325/163 | 275/135 |
|---|---|---|---|---|---|---|---|---|
| LHSV, $h_{-1}$ | 1.0 | 1.0 | 1.0 | 1.0 | 1.0 | 4.0 | 6.0 | 0.5 |
| Feed Composition | | | | | | | | |
| MeOH/EC, molar ratio | 4.0 | 4.0 | 4.0 | 4.0 | 4.0 | 4.0 | 4.0 | 4.0 |
| Total Liquid Product Composition | | | | | | | | |
| MeOH, wt % | 47.8 | 44.8 | 43.3 | 46.5 | 53.9 | 46.1 | 47.5 | 42.9 |
| EC, wt % | 18.8 | 16.5 | 14.8 | 16.2 | 12.0 | 18.8 | 20.2 | 13.9 |

TABLE 2-continued

Transesterification of Ethylene Carbonate with Methanol
Catalyzed by Pseudoboehmite Alumina (Condition: 100 psig)

| Temperature, ° F./° C. | 250/121 | 275/135 | 300/149 | 325/163 | 350/177 | 325/163 | 325/163 | 275/135 |
|---|---|---|---|---|---|---|---|---|
| HEMC Intermediate wt % | 10.0 | 7.3 | 5.9 | 3.0 | 1.7 | 4.9 | 5.3 | 6.9 |
| DMC, wt % | 15.0 | 19.1 | 22.0 | 19.1 | 18.4 | 18.2 | 16.6 | 22.6 |
| EG, wt % | 10.4 | 13.3 | 14.9 | 11.7 | 7.2 | 12.4 | 11.4 | 15.6 |
| DMC/EG, Molar Ratio | 1.00 | 0.99 | 1.02 | 1.13 | 1.76 | 1.01 | 1.00 | 1.00 |
| EC Conv., % | 36.0 | 46.4 | 53.2 | 55.5 | 69.1 | 44.8 | 40.8 | 54.0 |
| DMC Select., % | 100.0 | 98.9 | 99.1 | 81.5 | 60.8 | 98.1 | 98.0 | 99.3 |
| EG Select., % | 100.0 | 99.8 | 97.3 | 72.3 | 34.5 | 96.8 | 97.6 | 99.3 |

TABLE 3

Transesterification of Ethylene Carbonate with Methanol
Catalyzed by γ-Alumina (Condition: 100 psig)

| Temperature, ° F./° C. | 250/121 | 275/135 | 300/149 | 325/163 | 350/177 | 325/163 | 325/135 |
|---|---|---|---|---|---|---|---|
| LHSV, h$_{-1}$ | 1.0 | 1.0 | 1.0 | 1.0 | 1.0 | 4.0 | 6.0 |
| Feed Composition | | | | | | | |
| MeOH/EC, molar ratio | 4.0 | 4.0 | 4.0 | 4.0 | 4.0 | 4.0 | 4.0 |
| Total Liquid Product Composition | | | | | | | |
| MeOH, wt % | 50.9 | 49.6 | 48.0 | 52.5 | 57.3 | 51.0 | 52.5 |
| EC, wt % | 25.1 | 22.8 | 19.9 | 20.7 | 13.7 | 23.4 | 25.7 |
| HEMC Intermediate wt % | 8.8 | 6.9 | 3.8 | 1.6 | 0.9 | 2.8 | 3.1 |
| DMC, wt % | 8.7 | 12.3 | 16.6 | 12.2 | 12.5 | 12.8 | 10.5 |
| EG, wt % | 6.6 | 8.3 | 10.4 | 5.3 | 3.3 | 8.3 | 7.0 |
| DMC/EG, Molar Ratio | 0.91 | 1.02 | 1.10 | 1.59 | 2.61 | 1.06 | 1.04 |
| EC Conv., % | 22.8 | 30.4 | 43.8 | 47.4 | 67.2 | 35.9 | 29.4 |
| DMC Select., % | 91.2 | 99.1 | 91.9 | 60.6 | 41.6 | 88.0 | 88.1 |
| EG Select., % | 100.0 | 96.9 | 83.4 | 38.1 | 15.9 | 82.7 | 85.1 |

TABLE 4

Transesterification of Ethylene Carbonate with Methanol
Catalyzed by Cs-Alumina (Condition: 100 psig)

| Temperature, ° F./° C. | 250/121 | 275/135 | 300/149 | 325/163 | 350/177 | 325/163 | 325/135 |
|---|---|---|---|---|---|---|---|
| LHSV, h$_{-1}$ | 1.0 | 1.0 | 1.0 | 1.0 | 1.0 | 4.0 | 6.0 |
| Feed Composition | | | | | | | |
| MeOH/EC, molar ratio | 4.0 | 4.0 | 4.0 | 4.0 | 4.0 | 4.0 | 4.0 |
| Total Liquid Product Composition | | | | | | | |
| MeOH, wt % | 51.5 | 49.4 | 46.9 | 48.2 | 60.1 | 51.0 | 52.1 |
| EC, wt % | 24.5 | 21.8 | 18.9 | 18.0 | 17.4 | 24.1 | 25.7 |
| HEMC Intermediate wt % | 9.6 | 7.0 | 4.2 | 2.5 | 1.0 | 3.4 | 3.6 |
| DMC, wt % | 8.3 | 12.8 | 17.6 | 17.4 | 9.0 | 12.4 | 10.5 |
| EG, wt % | 6.1 | 8.8 | 11.5 | 10.4 | 2.4 | 8.2 | 7.0 |
| DMC/EG, Molar Ratio | 0.94 | 1.00 | 1.06 | 1.15 | 2.59 | 1.04 | 1.04 |
| EC Conv., % | 22.1 | 32.6 | 45.8 | 52.0 | 58.4 | 33.9 | 28.7 |
| DMC Select., % | 90.7 | 96.1 | 92.9 | 79.3 | 34.6 | 88.8 | 90.1 |
| EG Select., % | 96.6 | 95.7 | 87.9 | 68.7 | 13.4 | 85.1 | 87.1 |

The comparisons among the three catalysts are made under similar process conditions (feed ratio, pressure, LHSV, etc) and are shown in FIGS. 1–3. The results demonstrate that a good EC conversion is obtainable with a very high DMC/EG selectivity. Further, the high DMC/EG selectivity is observed over a wider temperature range than for conventional catalysts. An increase in EC conversion is observed with an increase in temperature.

Table 2 in particular, which relates to the performance of pseudoboehmite, shows that good EC conversion, and ≧98% DMC and EG selectivity are obtainable under optimal reaction conditions. Pseudoboehmite alumina (containing a larger amount of surface hydroxyl groups) exhibits higher activity and DMC/EG selectivity over a wide temperature range vs. γ-alumina and Cs-alumina. Apparently, hydroxyl groups play an important role in promoting the catalytic activity. The observed high selectivity of the hydrated alumina could be due to its low acidity, which inhibits side reactions such as dehydration of alkanols and subsequent hydrolysis of organic carbonates.

Therefore, the method of the invention is adaptable to commercial application because of the good level of activity, very high selectivity over a wide temperature range, and the stability and relatively low cost of the IIIA metal oxide catalyst used.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

We claim:

1. A method for co-producing dialkyl carbonate and alkanediol comprising reacting alkylene carbonate with alkanol under transesterfication process conditions in the presence of a catalyst consisting essentially of a IIIA metal oxide.

2. The method of claim 1 wherein said alkylene carbonate is ethylene carbonate and wherein said alkanol is methanol.

3. The method of claim 1 wherein said IIIA metal oxide is alumina.

4. The method of claim 3 wherein said alumina is selected from the group consisting of aluminum trihydroxide or aluminum monohydroxide.

5. The method of claim 4 wherein said aluminum monohydroxide is pseudoboehmite.

6. The method of claim 1 wherein at least a portion of said IIIA metal oxide catalyst has an octahedral structure.

7. The method of claim 1 wherein said IIIA metal oxide contains hydroxyl groups.

8. The method of claim 7 wherein said hydroxyl groups are present in an amount greater than 0.1 wt % and less than 30 wt % of said catalyst.

9. The method of claim 1 wherein said catalyst further comprises an inert catalyst support.

10. The method of claim 1 wherein said process conditions comprise a reaction temperature of about 20° C. to about 300° C., a reaction pressure of about 14 to about 4000 psig, a liquid hour space velocity of about 0.1 to about 40 $hr^{-1}$, and a molar ratio of alkanol to alkylene carbonate of about 1–20.

* * * * *